(12) United States Patent
Hyde et al.

(10) Patent No.: US 7,919,042 B2
(45) Date of Patent: Apr. 5, 2011

(54) STERILIZATION OF CONSUMABLE COMPOSITION DISPENSERS

(75) Inventors: Roderick A. Hyde, Redmond, WA (US); Eric C. Leuthardt, St. Louis, MO (US); Robert W. Lord, Seattle, WA (US); Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 569 days.

(21) Appl. No.: 12/012,500

(22) Filed: Feb. 1, 2008

(65) Prior Publication Data

US 2009/0142223 A1 Jun. 4, 2009

Related U.S. Application Data

(63) Continuation-in-part of application No. 12/006,252, filed on Dec. 31, 2007, and a continuation-in-part of application No. 12/004,094, filed on Dec. 19, 2007, and a continuation-in-part of application No. 12/002,794, filed on Dec. 18, 2007, and a continuation-in-part of application No. 12/001,063, filed on Dec. 7, 2007, now Pat. No. 7,804,419, and a continuation-in-part of application No. 12/001,061, filed on Dec. 7, 2007, and a continuation-in-part of application No. 11/998,461, filed on Nov. 29, 2007.

(51) Int. Cl.
| | | |
|---|---|---|
| *A61L 2/00* | (2006.01) | |
| *A61L 9/00* | (2006.01) | |
| *G05B 17/00* | (2006.01) | |
| *B65D 88/54* | (2006.01) | |
| *B67D 5/58* | (2006.01) | |
| *B01D 17/06* | (2006.01) | |
| *C02F 1/68* | (2006.01) | |
| *A23L 3/00* | (2006.01) | |
| *A21D 6/00* | (2006.01) | |
| *A24F 27/14* | (2006.01) | |
| *A23C 3/07* | (2006.01) | |
| *A23N 15/00* | (2006.01) | |

(52) U.S. Cl. ............... 422/24; 422/1; 422/3; 422/26; 422/28; 422/32; 422/116; 422/119; 422/292; 422/300; 222/321.7; 222/148; 222/190; 222/630; 222/526; 222/544; 210/748.01; 210/748.1; 210/748.11; 210/764; 426/234; 426/235; 426/248; 221/135; 99/451; 99/645

(58) Field of Classification Search ............... 422/1, 3, 422/24, 26, 28, 32, 116, 119, 292, 300; 222/321.7, 222/148, 190, 630, 526, 544; 210/748.01, 210/748.1, 748.11, 764; 426/234, 235, 248; 221/135; 99/451, 645

See application file for complete search history.

(56) References Cited

U.S. PATENT DOCUMENTS

| | | | |
|---|---|---|---|
| 5,408,443 A | 4/1995 | Weinberger | |
| 5,971,594 A | 10/1999 | Sahai et al. | |
| 6,054,928 A | 4/2000 | Lemelson et al. | |
| 6,182,453 B1 * | 2/2001 | Forsberg | 62/125 |
| 6,249,717 B1 | 6/2001 | Nicholson et al. | |
| 6,252,494 B1 | 6/2001 | Howell | |
| 6,490,920 B1 | 12/2002 | Netzer | |
| 6,625,518 B2 | 9/2003 | Depeursinge | |
| 6,636,780 B1 | 10/2003 | Haitin et al. | |
| 6,732,884 B2 | 5/2004 | Topliffe et al. | |
| 6,773,668 B1 | 8/2004 | Everson et al. | |
| 6,856,932 B1 * | 2/2005 | Wallace | 702/130 |
| 7,072,738 B2 | 7/2006 | Bonney et al. | |
| 7,440,818 B2 | 10/2008 | Handfield et al. | |
| 7,454,267 B2 | 11/2008 | Bonney et al. | |
| 7,502,664 B2 | 3/2009 | Berg | |
| 7,715,277 B2 | 5/2010 | de la Huerga | |
| 2002/0001535 A1 * | 1/2002 | Weng | 422/3 |
| 2003/0220608 A1 | 11/2003 | Huitt et al. | |
| 2004/0163970 A1 | 8/2004 | Sin et al. | |
| 2006/0259195 A1 | 10/2006 | Eliuk et al. | |
| 2007/0184219 A1 | 8/2007 | Johnson | |
| 2009/0057341 A1 | 3/2009 | Girard et al. | |

OTHER PUBLICATIONS

U.S. Appl. No. 11/998,461, filed Jun. 4, 2009, Leuthardt, et al.
U.S. Appl. No. 12/001,061, filed Jun. 11, 2009, Hyde, et al.
U.S. Appl. No. 12/001,063, filed Jun. 11, 2009, Hyde, et al.
U.S. Appl. No. 12/002,794, filed Jun. 4, 2009, Hyde, et al.
U.S. Appl. No. 12/004,094, filed Jun. 4, 2009, Hyde, et al.

U.S. Appl. No. 12/006,252, filed Jul. 2, 2009, Hyde, et al.
U.S. Appl. No. 12/074,245, filed Jun. 4, 2009, Haitin, et al.
U.S. Appl. No. 12/927,038, filed Nov. 4, 2010, Hyde et al.

* cited by examiner

*Primary Examiner* — Jill Warden
*Assistant Examiner* — Monzer R Chorbaji
(74) *Attorney, Agent, or Firm* — Suiter Swantz pc llo (57) ABSTRACT

Methods and systems for programmed dispensation of consumable compositions are provided.

A method for sterilizing a beverage container may comprise: (a) detecting a sterilization status of a beverage container; and (b) controlling functionality of a controllable device according to the sterilization status.

A system for sterilizing a beverage container may comprise: (a) detecting a sterilization status of a beverage container; and (b) controlling functionality of a controllable device according to the sterilization status.

A method for sterilizing a beverage container may comprise: (a) detecting an identity of a consumable composition; and (b) controlling a sterilization of at least a portion of a beverage container according to the identity of the consumable composition.

A system for sterilizing a beverage container may comprise: (a) detecting an identity of a consumable composition; and (b) controlling a sterilization of at least a portion of a beverage container according to the identity of the consumable composition.

16 Claims, 10 Drawing Sheets

STERILIZATION OF CONSUMABLE COMPOSITION DISPENSERS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/998,461, entitled Programmed Dispensing of Consumable Compositions, naming Eric C. Leuthardt, Clarence T. Tegreene, Lowell L. Wood, Jr., Roderick A. Hyde and Robert W. Lord as inventors, filed Nov. 29, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/001,061, entitled Programmed Dispensing of Consumable Compositions, naming Roderick A. Hyde, Eric C. Leuthardt, Robert W. Lord, Clarence T. Tegreene, and Lowell L. Wood, Jr. as inventors, filed Dec. 7, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/001,063, entitled Programmed Dispensing of Consumable Compositions, naming Roderick A. Hyde, Eric C. Leuthardt, Robert W. Lord, Clarence T. Tegreene, and Lowell L. Wood, Jr. as inventors, filed Dec. 7, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/002,794, entitled Communications Regarding Aspects of a Consumable Composition, naming Roderick A. Hyde, Eric C. Leuthardt, Robert W. Lord, Clarence T. Tegreene, and Lowell L. Wood, Jr. as inventors, filed Dec. 18, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/004,094, entitled Communications Regarding Aspects of a Consumable Composition, naming Roderick A. Hyde, Eric C. Leuthardt, Robert W. Lord, Clarence T. Tegreene, and Lowell L. Wood, Jr. as inventors, filed Dec. 19, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,252, entitled Sterilization of Consumable Composition Dispensers, naming Roderick A. Hyde, Eric C. Leuthardt, Robert W. Lord, Clarence T. Tegreene, and Lowell L. Wood, Jr. as inventors, filed Dec. 31, 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Programmed regimens of consumable compositions may be prescribed by a physician or may simply be desirable for the health and well-being of an individual. However, confusion may arise concerning the schedule, dosage, and/or compliance with a programmed dosing regimen.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
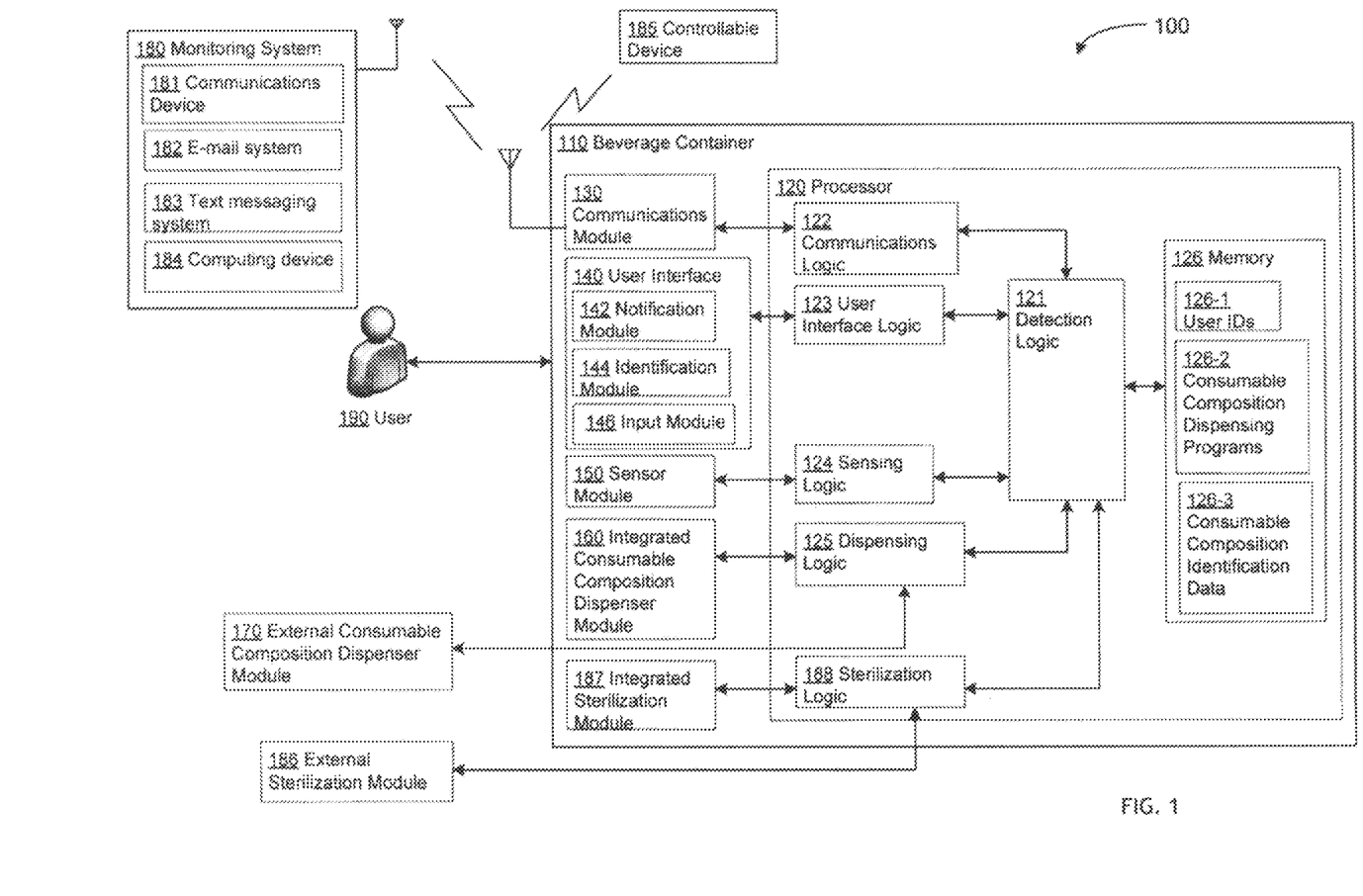
FIG. 1 shows a high-level block diagram of a beverage container.

FIG. 1 illustrates an example environment in which one or more technologies may be implemented. A consumable composition dispensing system 100 may comprise a beverage container 110 to be used by user 190. The beverage container 110 may be any receptacle configured for retaining a liquid or gel composition. For example, the beverage container 110 may include a cup, glass, mug, bowl, pitcher, jug, or the like.

The beverage container 110 may include a processor 120 (e.g. a microprocessor), a communications module 130 (e.g. a cellular transceiver, a Bluetooth transceiver, a WiFi transceiver, a satellite transceiver), a user interface 140 (e.g. display, touchscreen, keypad, speaker system), a sensor module 150 (e.g. a thermometer, barometer, concentration sensor, biometric sensor, accelerometer, UV sensor) an integrated consumable composition dispenser module 160 (e.g. injector, mechanical dispenser) and/or an integrated sterilization module 187 (e.g. a heating element).

The integrated consumable composition dispenser module 160 may be physically incorporated as a component of the beverage container 110. The integrated consumable composition dispenser module 160 may include an actuated mechanical apparatus which opens in response to a command from dispensing logic 125, thereby dispensing a dose of the consumable composition. The beverage container 110 may be configured to receive a dose of the consumable composition via gravitational flow or by pressurized injection of the dispensed composition from the integrated consumable composition dispenser module 160.

The external consumable composition dispenser module 170 may be physically separated from the beverage container 110. The external consumable composition dispenser module 170 may include a mechanical apparatus which opens in response to a command from dispensing logic 125 so as to introduce a dose of the consumable composition into the beverage container 110. The beverage container 110 may be configured to receive a dose of the consumable composition via a communicating assembly whereby the beverage container 110 may be physically coupled to the external consumable composition dispenser module 170 via a mutual conduit operably configured to allow the passage of the consumable composition between the external consumable composition dispenser module 170 and the beverage container 110.

Processor 120 may include communications logic 122, user interface logic 123, sensing logic 124, dispensing logic 125, memory 126, and/or sterilization logic 188.

Memory 126 may include user IDs 126-1, consumable composition dispensing programs 126-2, and/or consumable composition identification data 126-3.

User interface 140 may include a notification module 142 (e.g. an LED); an identification module 144 (a fingerprint scanner), and/or an input module 146 (a microphone).

Sensor module 150 may include one or more of a light source sensor, a position sensor, an emission sensor, a spectrophotometer, an infrared or ultraviolet sensor, a biometric sensor and the like. Sensor module 150 may include a biometric sensor which senses the presence of saliva, perspiration, sebum and the like, either on the surface of the beverage container 110 or as a component of the contents therein. Sensor module 150 may include an accelerometer, an inertial motion sensor, and the like, which may sense the movement of the beverage container 110. Sensor module 150 may include a fiber optic pressure sensor, mechanical deflection pressure sensor, strain gauge pressure sensor, piezoresistive pressure sensor, microelectromechanical (MEMS) pressure sensor, variable capacitance pressure sensor, and the like which senses a pressure applied to the beverage container 110. Sensor module 150 may include a capacitive concentration sensor which may sense a concentration of the consumable composition present in the beverage container 110. Sensor module 150 may include an inclinometer and the like. Sensor module 150 may include a flowmeter for sensing a flowrate into or out of the beverage container 110. Sensor module 150 may include a capacitive level sensor, such as a strip or dual-probe sensor (e.g., a strip running down that side of the cup to sense a fluid level based at least in part between differences in the known/inferred/assumed dielectric constants of air and a fluid). In some instances, the dielectric constant is recalled/calculated in response to a sensed composition of a fluid (e.g., sensed constituents of an alcoholic cocktail); in other instances, the dielectric constant is assumed (e.g., defaults to that of water). Sensor module 150 may include an electro-chemical analyzer (e.g. an electrode pair disposed within an electrolyte capable of measuring an electrochemical reaction) for measuring a concentration of a gas in an atmosphere. Sensor module 150 may include a chemical composition analysis mechanism (e.g. photoionization sensors, spectroscopic sensors, spectrometric sensors, crystallographic sensors, electrochemical sensors, calorimetric sensors).

The consumable composition dispensing system 100 may further include an external consumable composition dispenser module 170 (e.g. injector, mechanical dispenser) and/or external sterilization module 186 (e.g. an autoclave).

Monitoring system 180 may relay a notification (e.g. a notification that a sterilization of the beverage container 110 has occurred) received from communications module 130 to a communications device 181 (e.g. a cell phone, satellite phone, Blackberry®, and/or land-line phone), e-mail system 182 (e.g. an IMAP, POP3, SMTP, and/or HTTP e-mail server having an e-mail account associated with a user 190), text messaging system 183 (e.g. SMS system in GSM) and/or a computing device 184 (e.g. a personal digital assistant (PDA), personal computer, laptop, music player and/or gaming device).

The consumable composition may be a pharmaceutical composition including, but not limited to, one or more of the following: 5-alpha reductase inhibitors, 5-HT antagonists, ACE inhibitors, adrenergic agonists, adrenergic neurone blockers, alkalising agent, alpha blockers, aminoglycosides, anaesthetics, analgesics, androgens, angiotensin receptor blockers, anti-allergics, antiandrogens, antianginals, antiarrhythmics, antibiotics, anticholinergics, anticholinesterase, anticoagulants, anticonvulsants, antidepressants, antidiarrhoeals, antidopaminergics, anti-emetics, antiepileptics, anti-flatulents, antifungal, antifungals, anti-hemophilics, antihistamine, antihistamines, antiplatelets, antipsychotics, antiseptics, antispasmodic, antispasmodics, antithyroid drugs, antitussives, anxiolytics, astringents, barbiturates, benzodiazepine, beta-receptor antagonists, beta-receptor blocker, bile acid sequestrants, bronchodilators, calcitonins, calcium channel blockers, cannabinoids, carbonic anhydrase inhibitors/hyperosmotics, cardiac glycosides, cerumenolyti, cholinergics, corticosteroids, COX-2 selective inhibitors, cycloplegics, cyclopyrrolone, cytoprotectants, decongestants, diphosponates, diuretics, dopamine antagonist, emetic, fibrinolytics, fluoroquinolones, gonadotropins, growth hormones, H2-receptor antagonists, haemostatic drugs, heparins, hormonal contraceptives, hypnotics, hypolipidaemic agents, imidazoles, immunoglobulins, immunosuppressants, insulin, interferons, laxatives, local anesthetics, mast cell inhibitors, miotics, monoclonal antibodies, movement disorder drugs, mucolytics, muscle relaxants, mydriatics, neuromuscular drugs, nitrates, nitroglycerin, NSAIDs, ocular lubricants, opioids, parasympatholytics, parasympathomimetics, peripheral activators, polyenes, prostaglandin agonists/prostaglandin inhibitors, prostaglandin analogues, proton pump inhibitors, quinolones, reflux suppressants, selective alpha-1 blocker, sildenafil, statins, steroids, stimulants, sulfa drugs, sympathomimetics, thyroid hormones, topical anesthetics, topical antibiotics, vaccines, vasoconstrictors, vasodilators, vasopressin analogues, or the like.

The consumable composition may be a neutraceutical composition including, but not limited to, one or more of the following: vitamins (e.g., ascorbic acid, pyridoxine, riboflavin), minerals (e.g., calcium salts, zinc salts, potassium salts), hormones (e.g., dimethylaminoethanol (DMAE), dehydroepiandrosterone (DHEA), melatonin), biochemicals (e.g., adenosine triphosphate, coenzyme A, cysteine), glandulars (e.g., edible compositions derived from glandular organs of animals such as the thyroid, pancreas, adrenal cortex), herbals (e.g., ginkgo, garlic, goldenseal, echinacea), or the like.

Figure 2:
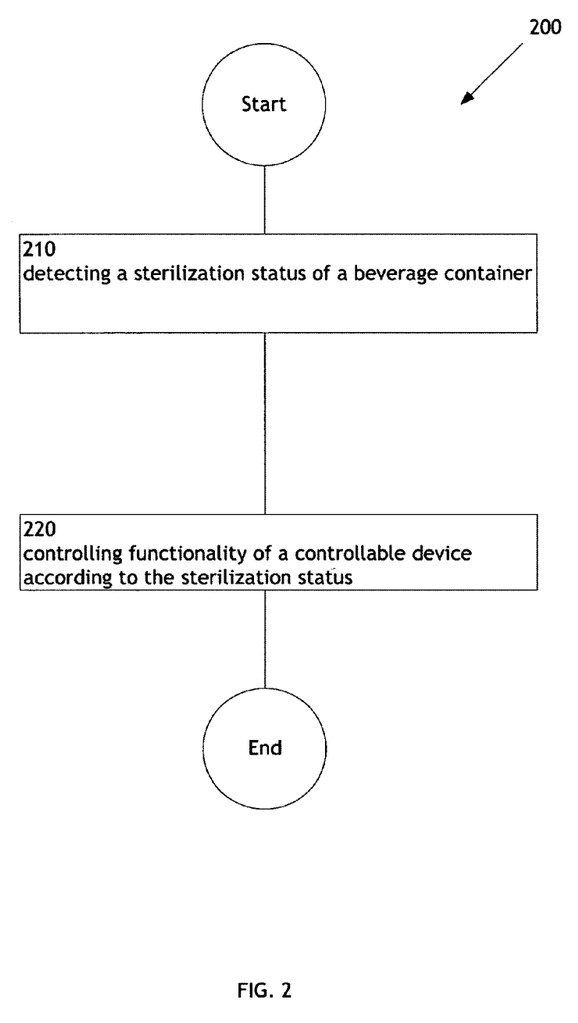
FIG. 2 is a high-level logic flowchart of a process.

FIG. 2 illustrates an operational flow 200 representing example operations related to sterilizing a beverage container. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to a detecting operation 210, where detecting a sterilization status of a beverage container may occur (e.g. determining whether a chemical sterilization has occurred within the previous three hours). For example, as shown in FIG. 1, the detection logic 121 may receive sterilization data from sterilization logic 188 operably coupled to the integrated sterilization module 187 or the external sterilization module 186. Upon receipt of sterilization data from the sterilization logic 188 indicating that a sterilization has occurred (e.g. a radiation, chemical or thermal sterilization), the detection logic 121 may update a sterilization status to reflect the sterilization.

In an alternate embodiment, detection logic 121 may receive sensor data from sensing logic 124 operably coupled to a sensor module 150. The sensor module 150 (e.g. a radiation sensor module, chemical sensor module, thermal sensor module) may detect a sterilization by the integrated sterilization module 187 or the external sterilization module 186. Upon receipt of sensor data from the sensing logic 124 indicating that a sterilization has occurred, the detection logic 121 may update a sterilization status to reflect the sterilization. Alternatively, the detection logic 121 may receive sensor data from sensing logic 124 indicating that one or more conditions indicate a sterile/unsterile condition (e.g., presence/absence of one or more bacteria, viruses, contaminants, etc.)

Then, in a controlling operation 220, controlling functionality of a controllable device according to the sterilization status may occur (e.g. opening an actuated aperture of the beverage container 110 to allow for the ingestion of its contents). For example, as shown in FIG. 1, the dispensing logic 125 may cause the integrated consumable composition dispenser 160 and/or the external consumable composition dispenser 170 to dispense a dose of consumable composition according to the sterilization status (e.g. the dispenser will only dispense a dose if a sterilization has occurred within a threshold amount of time).

Figure 3:
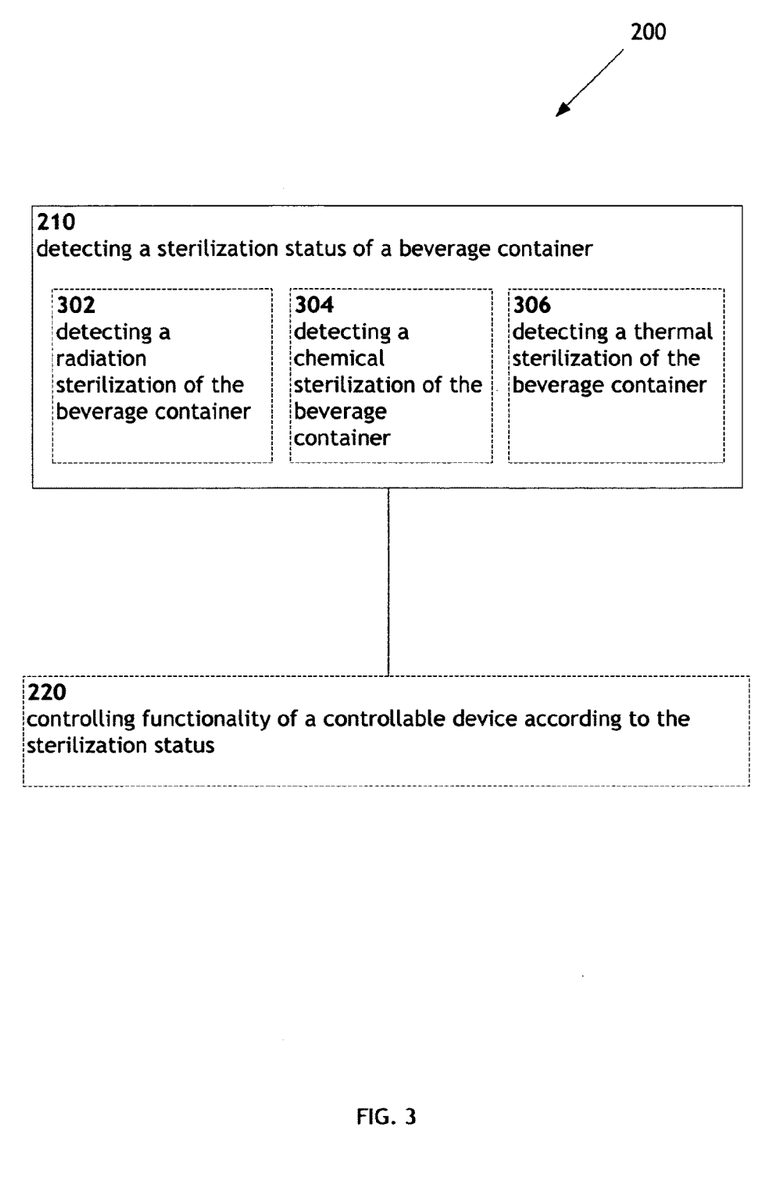
FIG. 3 is a high-level logic flowchart of a process depicting alternate implementations of FIG. 2.

FIG. 3 illustrates alternative embodiments of the example operational flow 200 of FIG. 2. FIG. 3 illustrates example embodiments where the detecting operation 210 may include at least one additional operation. Additional operations may include an operation 302, an operation 304, and/or an operation 306.

At the operation 302, detecting a radiation sterilization of the beverage container may occur (e.g. an ultraviolet sterilization). For example, as shown in FIG. 1, the sensor module 150 may be a radiation sensor module (e.g. an ultraviolet sensor). Upon detection of a radiation sterilization by the sensor module 150, the sensing logic 124 may provide sensor data to detection logic 121 so as to update a sterilization status of the beverage container 110.

At the operation 304, detecting a chemical sterilization of the beverage container may occur (e.g. an ozone sterilization). For example, as shown in FIG. 1, the integrated sterilization module 187 and/or the external sterilization module 186 may be chemical sterilization modules (e.g. ozone sterilization modules). Upon a chemical sterilization by the integrated sterilization module 187 and/or the external sterilization module 186, sterilization logic 188 may provide sterilization data to detection logic 121 so as to update a sterilization status of the beverage container.

At the operation 306, detecting a thermal sterilization of the beverage container may occur (e.g. heating via a heating element). For example, as shown in FIG. 1, the integrated sterilization module 187 and/or the external sterilization module 186 may be thermal sterilization modules (e.g. an autoclave). Upon a thermal sterilization by the integrated sterilization module 187 and/or the external sterilization module 186, sterilization logic 188 may provide sterilization data to detection logic 121 so as to update a sterilization status of the beverage container.

Figure 4:
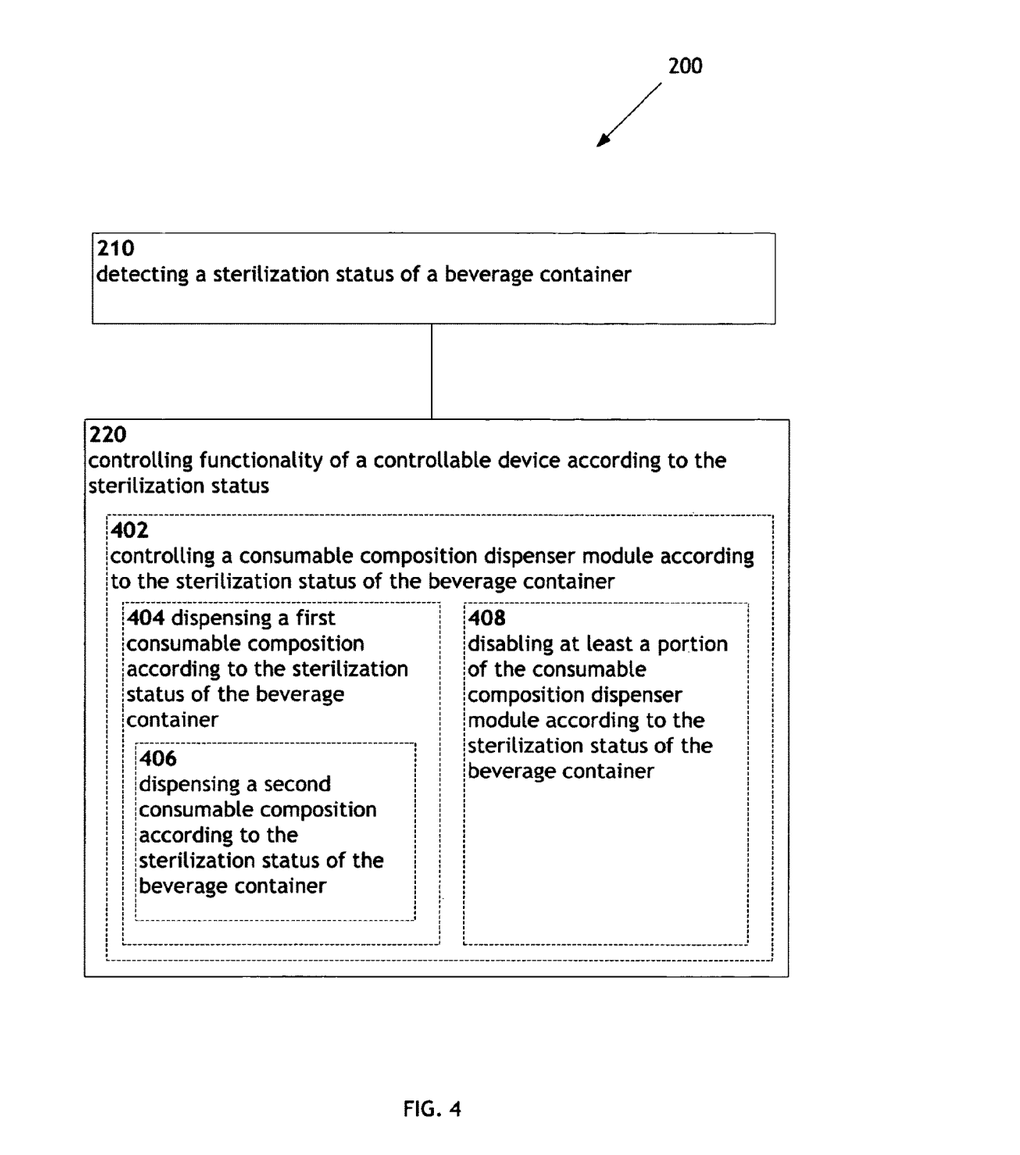
FIG. 4 is a high-level logic flowchart of a process.

FIG. 4 illustrates alternative embodiments of the example operational flow 200 of FIG. 2. FIG. 4 illustrates example embodiments where the controlling operation 220 may include at least one additional operation. Additional operations may include an operation 402, an operation 404, an operation 406, and/or an operation 408.

At the operation 402, controlling a consumable composition dispenser module according to the sterilization status of the beverage container may occur (e.g. providing power to an actuated dispensing mechanism). For example, as shown in FIG. 1, the dispensing logic 125 may cause the integrated consumable composition dispenser module 160 and/or the external consumable composition dispenser module 170 to dispense a dose of a consumable composition according to the sterilization status of the beverage container.

Further, at the operation 404, dispensing a first consumable composition according to the sterilization status of the beverage container may occur (e.g. dispensing a dose of an analgesic when the beverage container has been sterilized). For example, as shown in FIG. 1, the integrated consumable composition dispenser module 160 and/or the external consumable composition dispenser module 170 may dispense a dose of a consumable composition when sterilization logic 188 indicates that integrated sterilization module 187 or external sterilization module 186 has completed a sterilization.

Further, at the operation 406, dispensing a second consumable composition according to the sterilization status of the beverage container may occur (e.g. dispensing a dose of composition having an indicator color). For example, as shown in FIG. 1, the integrated consumable composition dispenser module 160 and/or the external consumable composition dispenser module 170 may dispense a dose of a second consumable composition (e.g. a dye, a neutralizing agent for a first consumable composition) when sterilization logic 188 indicates that a sterilization by the integrated sterilization module 187 or external sterilization module 186 has not been completed or has failed.

Further, at the operation 408, disabling at least a portion of the consumable composition dispenser module according to the sterilization status of the beverage container may occur (e.g. removing power from a consumable composition injection mechanism when a sterilization has not occurred). For example, as shown in FIG. 1, the dispensing logic 125 may cause the integrated consumable composition dispenser module 160 and/or the external consumable composition dispenser module 170 to withhold dispensation of a dose of a consumable composition when sensing logic 124 indicates that a sterilization by the integrated sterilization module 187 or external sterilization module 186 has not been completed or has failed.

Figure 5:
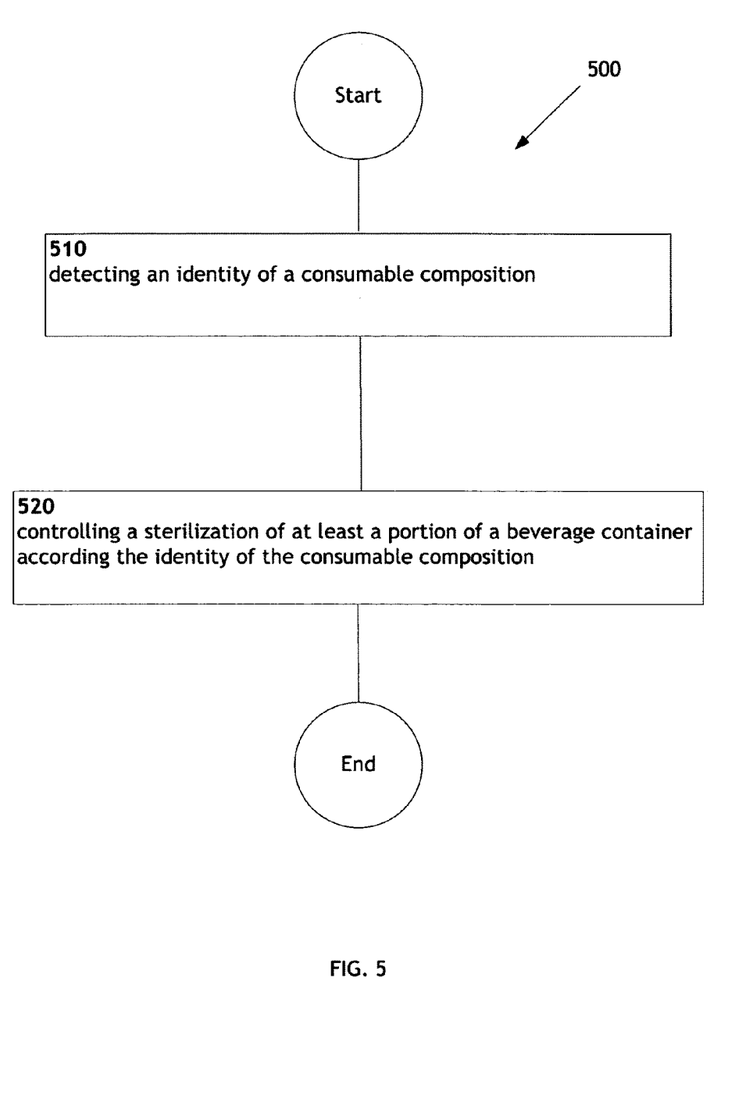
FIG. 5 is a high-level logic flowchart of a process depicting alternate implementations of FIG. 4.

FIG. 5 illustrates an operational flow 500 representing example operations related to sterilizing a beverage container. In FIG. 5 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 500 moves to a detecting operation 510, where detecting an identity of a consumable composition may occur (e.g. spectroscopic measurement of the composition of a biochemical). For example, as shown in FIG. 1, the sensing logic 124 may cause sensor module 150 to detect an identity (e.g. a chemical composition) of a consumable composition. Sensor module 150 may include a chemical composition analysis mechanism (e.g. photoionization sensors, spectroscopic sensors, spectrometric sensors, crystallographic sensors, electrochemical sensors, calorimetric sensors).

Then, in a controlling operation 520, controlling a sterilization of at least a portion of a beverage container according to the identity of the consumable composition may occur (e.g. deactivating one or more radiation sources in a radiation sterilization module when a radiation-sensitive consumable composition is dispensed). For example, as shown in FIG. 1, the sterilization logic 188 may cause the integrated sterilization module 187 and/or the external sterilization module 186 to sterilize selected portions of the beverage container according to an identity of a consumable composition.

Figure 6:
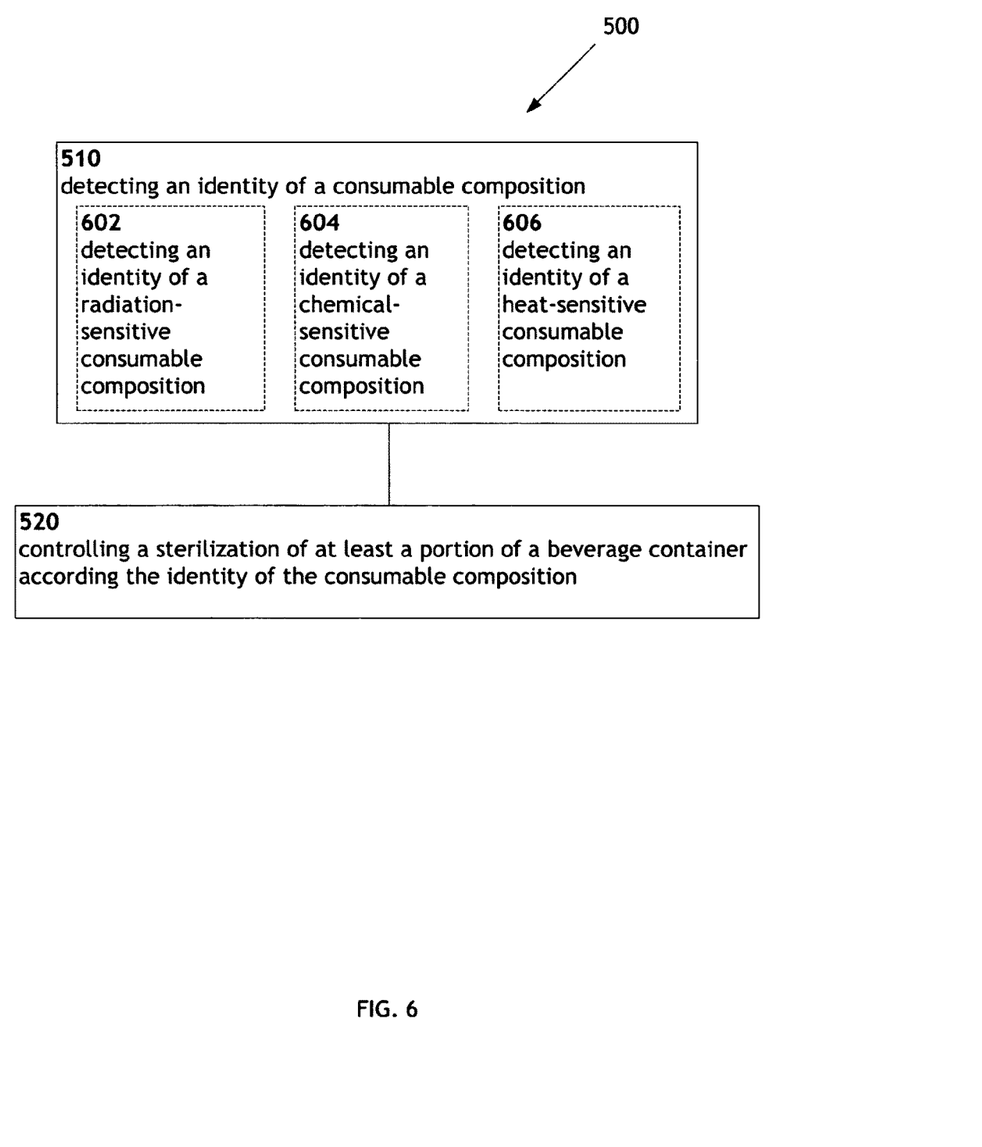
FIG. 6 is a high-level logic flowchart of a process depicting alternate implementations of FIG. 4.

FIG. 6 illustrates alternative embodiments of the example operational flow 500 of FIG. 5. FIG. 6 illustrates example embodiments where the detecting operation 510 may include at least one additional operation. Additional operations may include an operation 602, an operation 604, and/or an operation 606.

At the operation 602, detecting an identity of a radiation-sensitive consumable composition may occur (e.g. electrochemical detection of a consumable composition whose functionality may be affected by radiation sterilization). For example, as shown in FIG. 1, the sensor module 150 may detect a chemical composition of a radiation sensitive consumable composition which may be compared to consumable composition identification data 126-3 maintained in memory 126. Radiation sensitive consumable compositions may include, but are not limited to, substituted (e.g. sulfonic acid or sulfonate substituted) aminotriarylacetonitrile compositions, microencapsulated activator-drug precursor pairs, psoralen and psoralen derivatives, and the like, which may be sensitive to ultraviolet, x-ray and/or gamma ray radiation.

At the operation 604, detecting an identity of a chemical-sensitive consumable composition may occur (e.g. photoionization detection of a consumable composition whose functionality may be affected by chemical sterilization. For example, as shown in FIG. 1, the sensor module 150 may detect a chemical composition of a chemical-sensitive consumable composition which may be compared to consumable composition identification data 126-3 maintained in memory 126. Chemical-sensitive consumable compositions may include, but are not limited to, drug/carrier complexes having acid-sensitive spacers between the drug and carrier enabling the release of an active drug from the carrier in the presence of an acid.

At the operation 606, detecting an identity of a heat-sensitive consumable composition may occur (e.g. crystalographic detection of a consumable composition whose functionality may be affected by thermal sterilization. For example, as shown in FIG. 1, the sensor module 150 may detect a chemical composition of a heat-sensitive consumable composition which may be compared to consumable composition identification data 126-3 maintained in memory 126. A heat sensitive consumable composition may include heat-sensitive retrovirals (e.g. Ritonavir), epinephrine, diazepam, naloxone, and the like.

Figure 7:
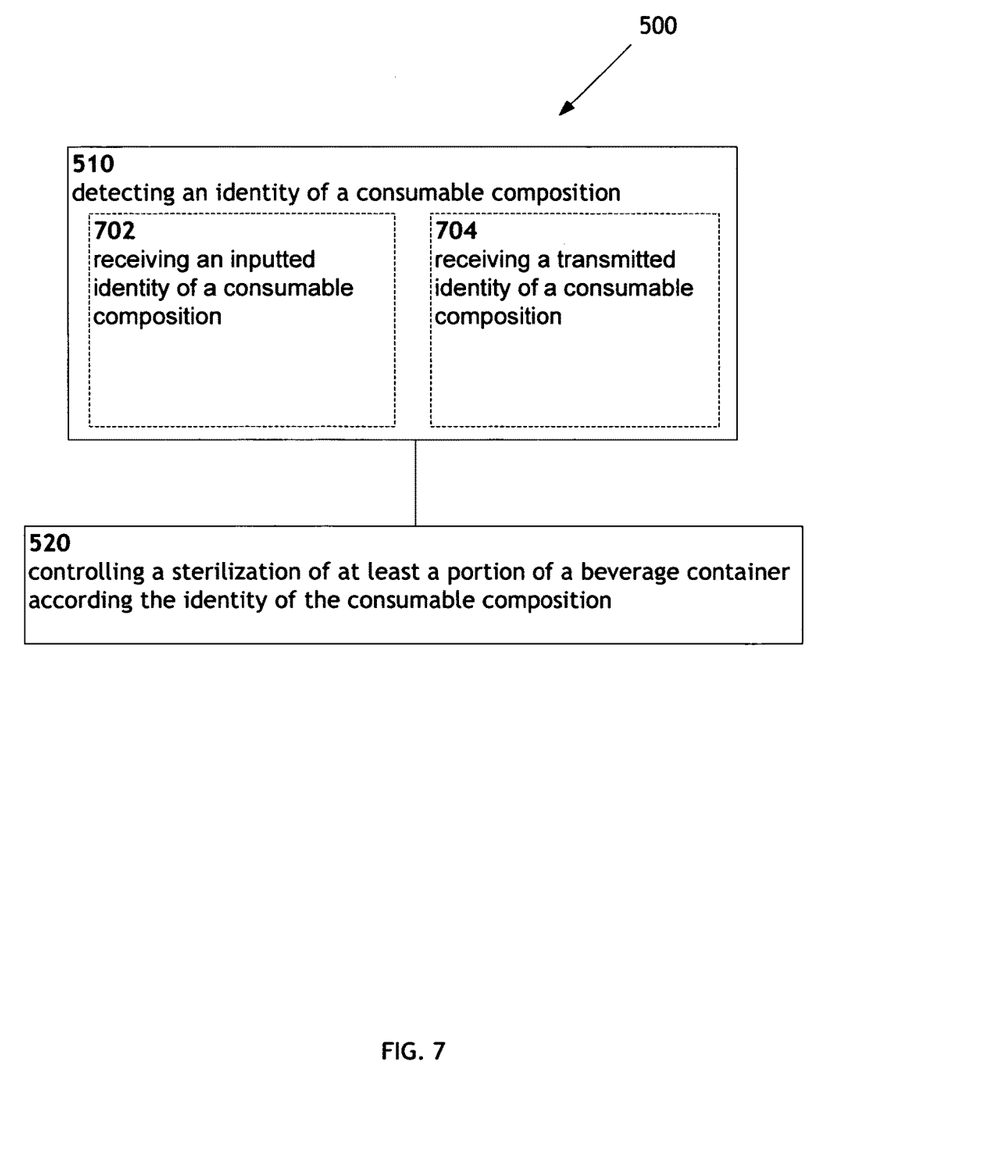
FIG. 7 is a high-level logic flowchart of a process depicting alternate implementations of FIG. 4.

FIG. 7 illustrates alternative embodiments of the example operational flow 500 of FIG. 5. FIG. 7 illustrates example embodiments where the detecting operation 510 may include at least one additional operation. Additional operations may include an operation 702, an operation 704, and/or an operation 606.

At the operation 702, receiving an inputted identity of a consumable composition may occur (e.g. receipt of a user input identifying a consumable composition whose functionality may be affected by a chemical sterilization agent). For example, as shown in FIG. 1, a user 190 may input an identity of a chemical-sensitive consumable composition via an input module 146 (e.g. a touch screen) of a user interface 140.

At operation 704, receiving a transmitted identity of a consumable composition may occur (e.g. receipt of identification data from a physician identifying a consumable composition whose functionality may be affected by thermal sterilization). For example, as shown in FIG. 1, the communications module 130, may receive consumable composition identification data from a monitoring system 180 (e.g. a system associated with a physician, a system associated with a consumable composition supply entity, and the like).

Figure 8:
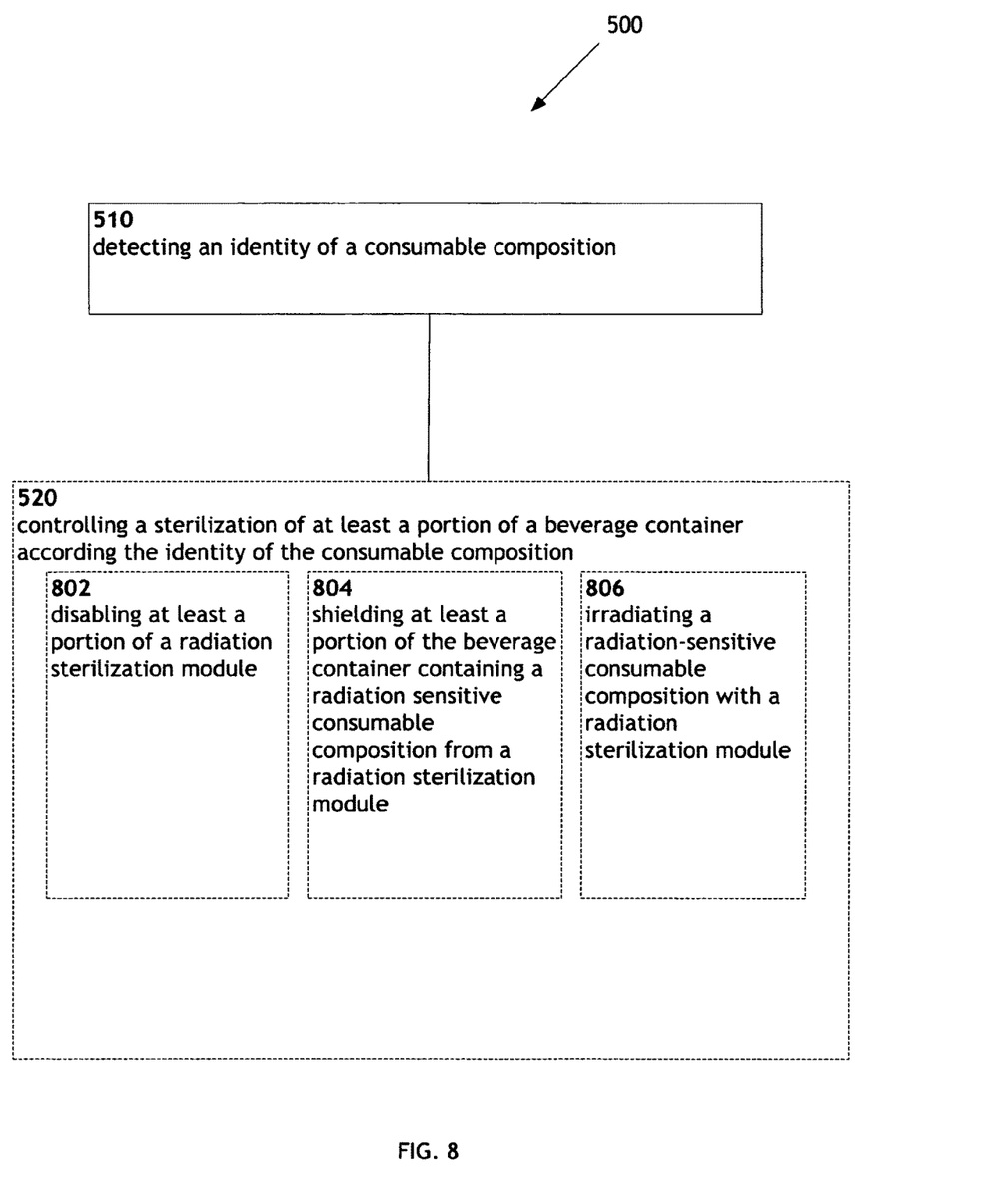
FIG. 8 is a high-level logic flowchart of a process depicting alternate implementations of FIG. 4.

FIG. 8 illustrates alternative embodiments of the example operational flow 500 of FIG. 5. FIG. 8 illustrates example embodiments where the controlling operation 520 may include at least one additional operation. Additional operations may include an operation 802, an operation 804 and an operation 806.

At the operation 802, disabling at least a portion of a radiation sterilization module may occur (e.g. removing power from one or more radiation sources). For example, as shown in FIG. 1, the sterilization logic 188 may cause the integrated sterilization module 187 and/or the external sterilization module 186 to forgo scheduled or requested radiation sterilization if a consumable composition previously dispensed or to be dispensed is adversely sensitive to radiation.

At the operation 804, shielding at least a portion of the beverage container containing a radiation sensitive consumable composition from a radiation sterilization module may occur (e.g. disposing a radiation-absorbing material between a radiation source and a consumable composition which may be damaged or deactivated by radiation). For example, as shown in FIG. 1, a portion of the beverage container 110 containing a consumable composition for which radiation may have a detrimental effect may be partitioned from a portion of the beverage container 110 to be sterilized by a radiation absorbing material.

At the operation 806, irradiating a radiation-sensitive consumable composition with a radiation sterilization module may occur (e.g. exposure of a consumable composition whose functionality is activated by radiation). For example, as shown in FIG. 1, sterilization logic 188 may cause the integrated sterilization module 187 and/or the external sterilization module 186 to irradiate at least a portion of the beverage container 110, the integrated consumable composition dispenser module 160 and/or the external consumable composition dispenser module 170 containing a consumable composition having functionality that is activated by radiation.

Figure 9:
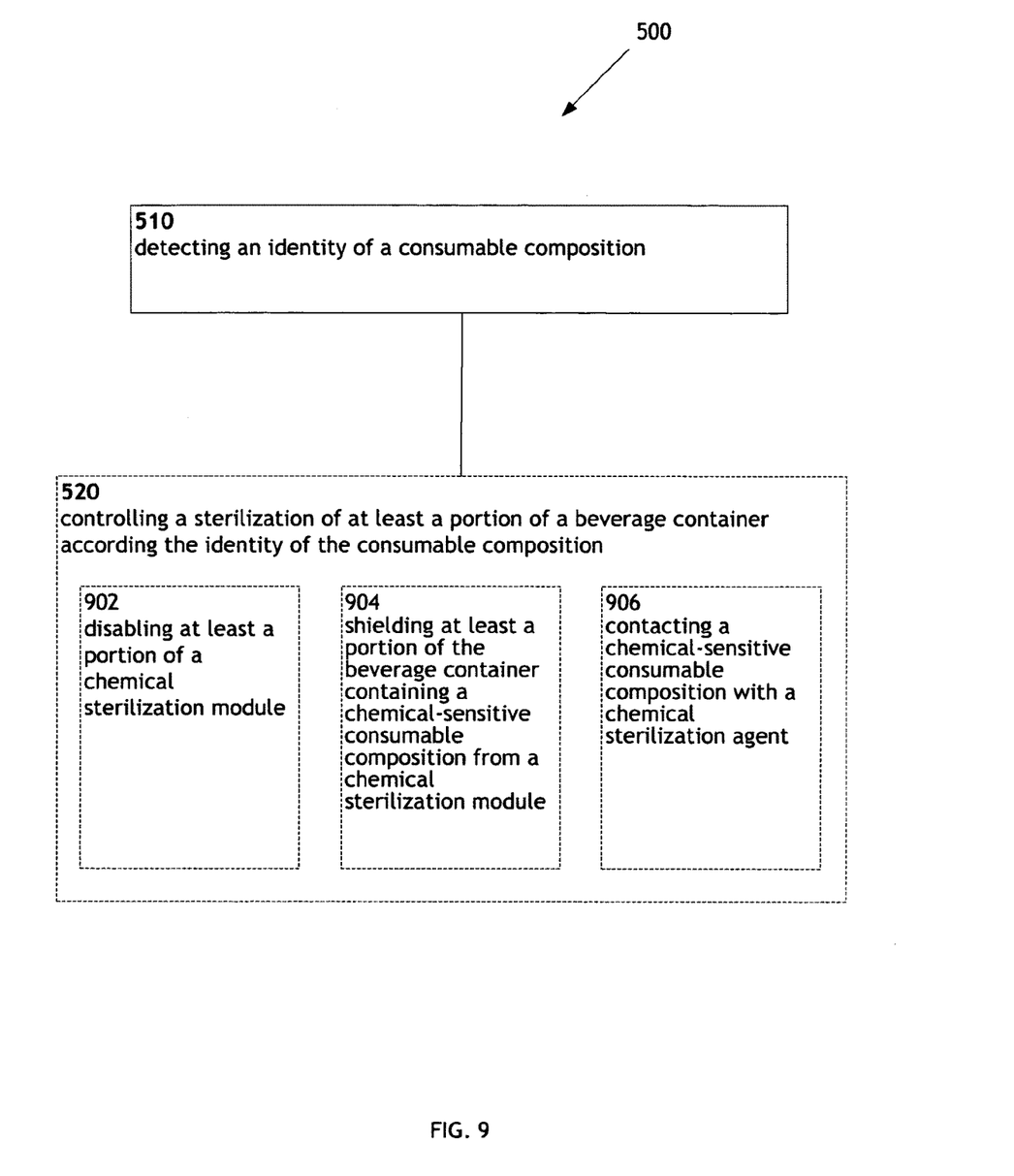
FIG. 9 is a high-level logic flowchart of a process depicting alternate implementations of FIG. 4.

FIG. 9 illustrates alternative embodiments of the example operational flow 500 of FIG. 5. FIG. 9 illustrates example embodiments where the controlling operation 520 may include at least one additional operation. Additional operations may include an operation 902, an operation 904 and an operation 906.

At the operation 902, disabling at least a portion of a chemical sterilization module may occur (e.g. removing power to at least one chemical sterilization agent dispenser). For example, as shown in FIG. 1, the sterilization logic 188 may cause the integrated sterilization module 187 and/or the external sterilization module 186 to forgo scheduled or requested chemical sterilization if a consumable composition previously dispensed or to be dispensed has functionality that may be affected (e.g. modified, inhibited) by a chemical sterilization agent.

At the operation 904, shielding at least a portion of the beverage container containing a chemical-sensitive consumable composition from a chemical sterilization module may occur (e.g. retaining a chemical-sensitive consumable composition in an gas-impermeable or liquid-impermeable microcapsule). For example, as shown in FIG. 1, the dispensing logic 188 may cause the integrated consumable composition dispenser module 160 and/or the external consumable composition dispenser module 170 to dispense a microencapsulated version of a consumable composition when the base consumable composition has functionality that may be affected (e.g. modified, inhibited) by a chemical sterilization agent.

At the operation 902, contacting a chemical-sensitive consumable composition with a chemical sterilization agent may occur (e.g. dispensing a drug/carrier complex having acid-sensitive spacers between the drug and carrier and an acid composition). For example, as shown in FIG. 1, the dispensing logic 188 may cause the integrated consumable composition dispenser module 160 and/or the external consumable composition dispenser module 170 to dispense a an acid composition and an acid-sensitive consumable composition which has functionality that may be affected (e.g. activated, modified, enhanced) by a chemical sterilization agent.

Figure 10:
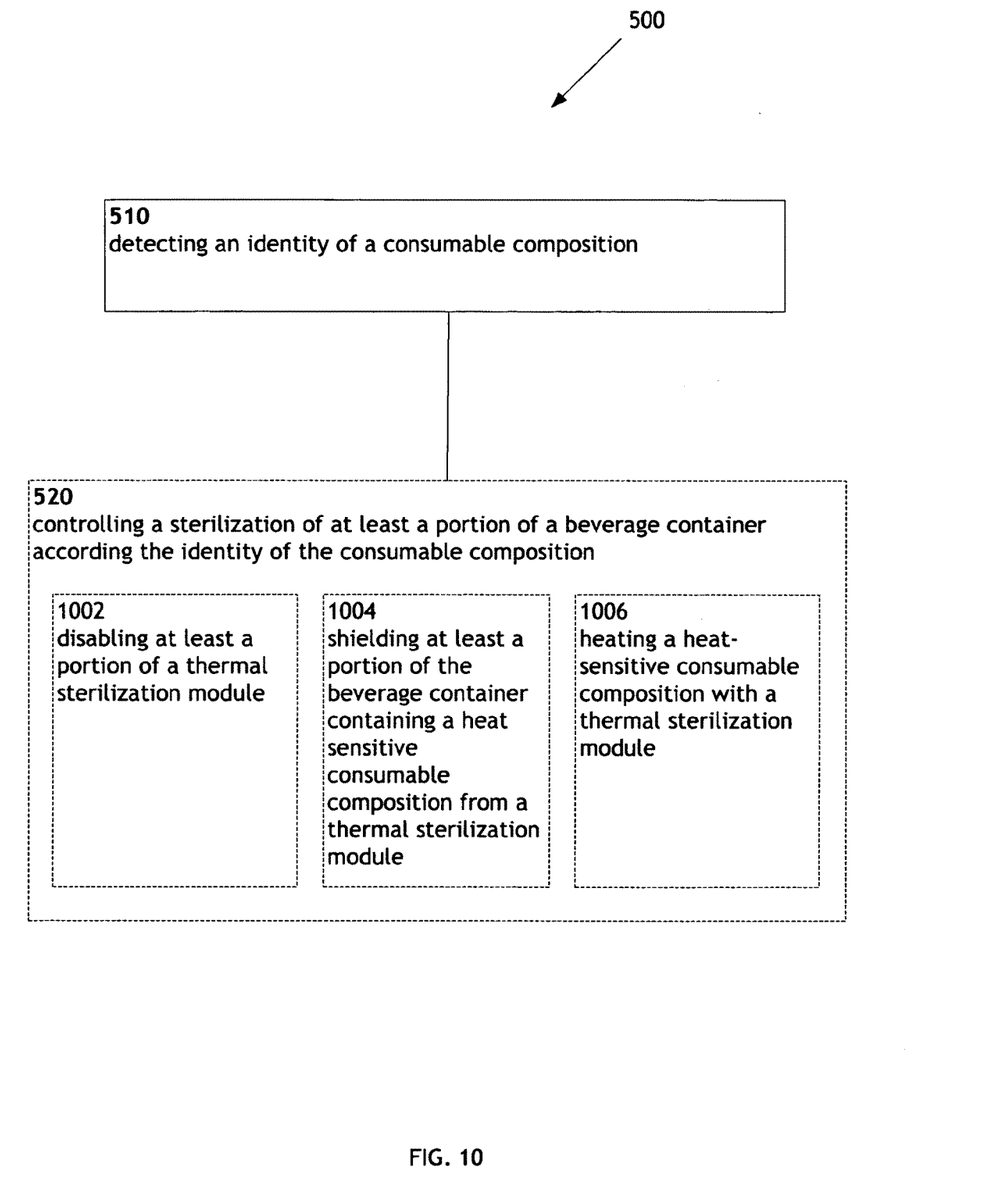
FIG. 10 is a high-level logic flowchart of a process depicting alternate implementations of FIG. 4.

FIG. 10 illustrates alternative embodiments of the example operational flow 500 of FIG. 5. FIG. 10 illustrates example embodiments where the controlling operation 520 may include at least one additional operation. Additional operations may include an operation 1002, an operation 1004, and/or an operation 1006.

At the operation 1002, disabling at least a portion of a thermal sterilization module may occur (e.g. removing power to at least one heating element). For example, as shown in FIG. 1, the sterilization logic 188 may cause the integrated sterilization module 187 and/or the external sterilization module 186 to forgo scheduled or requested thermal sterilization if a consumable composition previously dispensed or to be dispensed has functionality that may be affected (e.g. modified, inhibited) by exposure to thermal energy.

At the operation 1004, shielding at least a portion of the beverage container containing a heat sensitive consumable composition from a thermal sterilization module may occur (e.g. disposing a heat-absorbing material between a radiation source and a consumable composition which may be damaged or deactivated by thermal sterilization). For example, as shown in FIG. 1, a portion of the beverage container 110 containing a consumable composition for which thermal sterilization may have a detrimental effect may be partitioned from a portion of the beverage container 110 to be sterilized by a radiation absorbing material.

At the operation 1006, heating a heat-sensitive consumable composition with a thermal sterilization module may occur (e.g. exposure of a consumable composition whose functionality is activated by heat). For example, as shown in FIG. 1, sterilization logic 188 may cause the integrated sterilization module 187 and/or the external sterilization module 186 to heat at least a portion of the beverage container 110, the integrated consumable composition dispenser module 160 and/or the external consumable composition dispenser module 170 containing a consumable composition having functionality which is activated and/or enhanced by heating.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise. While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

Although user 190 is shown/described herein as a single illustrated figure, those skilled in the art will appreciate that user 190 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

What is claimed is:

1. A method for sterilizing a consumable composition dispenser, the method comprising:
    detecting an identity of a consumable composition; and
    controlling a sterilization of at least a portion of a beverage container according to the identity of the consumable composition, wherein the controlling a sterilization of at least a portion of a beverage container according to the identity of the consumable composition further comprises: shielding at least a portion of the beverage container containing a radiation sensitive consumable composition from a radiation sterilization module.

2. A system for sterilizing a consumable composition dispenser, the system comprising:
    means for detecting an identity of a consumable composition; and
    means for controlling a sterilization of at least a portion of a beverage container according to the identity of the consumable composition, wherein the means for controlling a sterilization of at least a portion of a beverage container according to the identity of the consumable composition further comprises: means for shielding at least a portion of the beverage container containing a radiation sensitive consumable composition from a radiation sterilization module.

3. The system of claim 2, wherein the means for detecting an identity of a consumable composition further comprises:
    means for detecting an identity of a radiation-sensitive consumable composition.

4. The system of claim 2, wherein the means for detecting an identity of a consumable composition further comprises:
    means for detecting an identity of a chemical-sensitive consumable composition.

5. The system of claim 2, wherein the means for detecting an identity of a consumable composition further comprises:
    means for detecting an identity of a heat-sensitive consumable composition.

6. The system of claim 2, wherein the means for detecting an identity of a consumable composition further comprises:
  means for receiving an inputted identity of a consumable composition.

7. The system of claim 2, wherein the means for detecting an identity of a consumable composition further comprises:
  means for receiving a transmitted identity of a consumable composition.

8. The system of claim 2, wherein the means for controlling a sterilization of at least a portion of a beverage container according to the identity of the consumable composition further comprises:
  means for disabling at least a portion of a radiation sterilization module.

9. The system of claim 2, wherein the means for controlling a sterilization of at least a portion of a beverage container according to the identity of the consumable composition further comprises:
  means for irradiating a radiation-sensitive consumable composition with a radiation sterilization module.

10. The system of claim 2, wherein the means for controlling a sterilization of at least a portion of a beverage container according to the identity of the consumable composition further comprises:
  means for disabling at least a portion of a chemical sterilization module.

11. The system of claim 2, wherein the means for controlling a sterilization of at least a portion of a beverage container according to the identity of the consumable composition further comprises:
  means for contacting a chemical-sensitive consumable composition with a chemical sterilization agent.

12. The system of claim 2, wherein the means for controlling a sterilization of at least a portion of a beverage container according to the identity of the consumable composition further comprises:
  means for disabling at least a portion of a thermal sterilization module.

13. The system of claim 2, wherein the means for controlling a sterilization of at least a portion of a beverage container according to the identity of the consumable composition further comprises:
  means for heating a heat-sensitive consumable composition with a thermal sterilization module.

14. A system for sterilizing a consumable composition dispenser, the system comprising:
  means for detecting an identity of a consumable composition; and
  means for controlling a sterilization of at least a portion of a beverage container according to the identity of the consumable composition, wherein the means for controlling a sterilization of at least a portion of a beverage container according to the identity of the consumable composition further comprises: means for shielding at least a portion of the beverage container containing a chemical-sensitive consumable composition from a chemical sterilization module.

15. A system for sterilizing a consumable composition dispenser, the system comprising:
  means for detecting an identity of a consumable composition; and
  means for controlling a sterilization of at least a portion of a beverage container according to the identity of the consumable composition, wherein the means for controlling a sterilization of at least a portion of a beverage container according to the identity of the consumable composition further comprises: means for shielding at least a portion of the beverage container containing a heat sensitive consumable composition from a thermal sterilization module.

16. A system for sterilizing a consumable composition dispenser, the system comprising:
  circuitry for detecting an identity of a consumable composition;
  circuitry for controlling a sterilization of at least a portion of a beverage container according to the identity of the consumable composition, wherein the circuitry for controlling a sterilization of at least a portion of a beverage container according to the identity of the consumable composition further comprises: circuitry for shielding at least a portion of the beverage container containing a radiation sensitive consumable composition from a radiation sterilization module.

* * * * *